US008080170B2

(12) United States Patent
Dams et al.

(10) Patent No.: US 8,080,170 B2
(45) Date of Patent: Dec. 20, 2011

(54) CATIONIC FLUORINATED ETHER SILANE COMPOSITIONS AND RELATED METHODS

(75) Inventors: Rudolf J. Dams, Antwerp (BE); Suresh Iyer, Woodbury, MN (US); Thomas P. Klun, Lakeland, MN (US); Chetan P. Jariwala, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 29 days.

(21) Appl. No.: 12/681,159

(22) PCT Filed: Sep. 22, 2008

(86) PCT No.: PCT/US2008/077195
§ 371 (c)(1),
(2), (4) Date: Apr. 1, 2010

(87) PCT Pub. No.: WO2009/045771
PCT Pub. Date: Apr. 9, 2009

(65) Prior Publication Data
US 2010/0219367 A1    Sep. 2, 2010

Related U.S. Application Data

(60) Provisional application No. 60/976,510, filed on Oct. 1, 2007.

(51) Int. Cl.
D06M 15/53 (2006.01)
C07F 7/10 (2006.01)
(52) U.S. Cl. ..................... 252/8.62; 556/413
(58) Field of Classification Search ............. 252/8.62; 556/413
See application file for complete search history.

(56) References Cited

U.S. PATENT DOCUMENTS

| | | | |
|---|---|---|---|
| 3,012,006 A * | 12/1961 | Holbrook et al. | 428/391 |
| 3,250,807 A | 5/1966 | Fritz et al. | |
| 3,250,808 A | 5/1966 | Moore, Jr. et al. | |
| 3,450,738 A * | 6/1969 | Blochl | 556/413 |
| 3,700,844 A | 10/1972 | Domba | |
| 3,810,874 A | 5/1974 | Mitsch et al. | |
| 3,810,875 A | 5/1974 | Rice et al. | |
| 3,817,739 A * | 6/1974 | Abbott et al. | 504/153 |
| 3,882,193 A | 5/1975 | Rice et al. | |
| 4,005,024 A * | 1/1977 | Rodriguez et al. | 510/514 |
| 4,321,404 A | 3/1982 | Williams et al. | |
| 4,417,066 A * | 11/1983 | Westall | 556/425 |
| 4,467,013 A * | 8/1984 | Baldwin | 442/81 |
| 4,645,813 A | 2/1987 | Fong | |
| 5,086,123 A | 2/1992 | Guenthner et al. | |
| 5,145,596 A * | 9/1992 | Blank et al. | 510/513 |
| 5,674,961 A | 10/1997 | Fitzgerald | |
| 5,739,369 A * | 4/1998 | Matsumura et al. | 556/425 |
| 5,753,569 A | 5/1998 | Michels et al. | |
| 5,798,415 A | 8/1998 | Corpart et al. | |
| 5,919,527 A | 7/1999 | Fitzgerald et al. | |
| 5,959,014 A * | 9/1999 | Liebeskind et al. | 524/389 |
| 6,037,429 A | 3/2000 | Linert et al. | |
| 6,111,043 A | 8/2000 | Corpart et al. | |
| 6,113,978 A | 9/2000 | Ornstein et al. | |
| 6,197,382 B1 | 3/2001 | Ornstein et al. | |
| 6,200,684 B1 * | 3/2001 | Yamaguchi et al. | 428/447 |
| 6,271,289 B1 | 8/2001 | Longoria et al. | |
| 6,303,190 B1 | 10/2001 | Linert et al. | |
| 6,326,447 B1 | 12/2001 | Fitzgerald | |
| 6,383,569 B2 | 5/2002 | Ornstein et al. | |
| 6,518,380 B2 | 2/2003 | Juhue et al. | |
| 6,540,866 B1 | 4/2003 | Zhang et al. | |
| 6,559,111 B2 * | 5/2003 | Colurciello et al. | 510/238 |
| 6,613,860 B1 | 9/2003 | Dams et al. | |
| 6,632,805 B1 | 10/2003 | Liebeskind et al. | |
| 6,649,272 B2 | 11/2003 | Moore et al. | |
| 6,762,172 B1 * | 7/2004 | Elfersy et al. | 514/63 |
| 6,861,149 B2 * | 3/2005 | Pellerite et al. | 428/428 |
| 6,923,921 B2 | 8/2005 | Flynn et al. | |
| 7,097,910 B2 | 8/2006 | Moore et al. | |
| 2001/0020077 A1 | 9/2001 | Juhue et al. | |
| 2002/0071959 A1 * | 6/2002 | Yamaguchi et al. | 428/447 |
| 2002/0090515 A1 * | 7/2002 | Pellerite et al. | 428/406 |
| 2002/0096286 A1 | 7/2002 | Kantamneni et al. | |
| 2002/0192380 A1 * | 12/2002 | Elsbernd et al. | 427/314 |
| 2003/0105263 A1 * | 6/2003 | Fan et al. | 528/30 |
| 2003/0113555 A1 * | 6/2003 | Pellerite et al. | 428/447 |
| 2003/0168783 A1 | 9/2003 | Dams | |
| 2003/0224112 A1 | 12/2003 | Dams | |
| 2004/0044139 A1 | 3/2004 | Grootaert et al. | |

(Continued)

FOREIGN PATENT DOCUMENTS

EP        1 225 187 A1        7/2002

(Continued)

OTHER PUBLICATIONS

Shao et al. Journal of Fluorine Chemistry, 2004, 125, 721-724.*
AATCC Test Method 22-2001, "Water Repellency: Spray Test", (2002), pp. 65-67, AATCC Technical Manual.
AATCC Test Method 118-1983, "Oil Repellency: Hydrocarbon Resistance Test", 1 page, AATCC Technical Manual.

(Continued)

*Primary Examiner* — Robert Loewe
(74) *Attorney, Agent, or Firm* — Lisa P. Fulton; James E. Garbe

(57) ABSTRACT

Compositions comprising cationic compounds having fluorinated ether groups and silane groups are provided, the compounds having the formula (I).

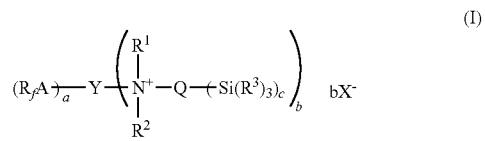

25 Claims, No Drawings

| U.S. PATENT DOCUMENTS | | |
|---|---|---|
| 2004/0077758 A1 | 4/2004 | Juhue et al. |
| 2004/0077775 A1 | 4/2004 | Audenaert et al. |
| 2005/0136264 A1 | 6/2005 | Dams et al. |
| 2010/0219367 A1 | 9/2010 | Dams et al. |
| 2010/0221967 A1 | 9/2010 | Iyer et al. |
| 2011/0045270 A1 | 2/2011 | Dams et al. |

| FOREIGN PATENT DOCUMENTS | | | |
|---|---|---|---|
| WO | WO 9742200 A1 | * | 11/1997 |
| WO | WO 9903866 A1 | * | 1/1999 |
| WO | 01/30873 A1 | | 5/2001 |
| WO | 03/018508 A1 | | 3/2003 |

* cited by examiner

CATIONIC FLUORINATED ETHER SILANE COMPOSITIONS AND RELATED METHODS

CROSS REFERENCE TO RELATED APPLICATIONS

This application is a national stage filing under 35 U.S.C. 371 of PCT/US2008/077195, filed Sep. 22, 2008, which claims priority to Provisional Application No. 60/976,510, filed Oct. 1, 2007, the disclosure of which is incorporated by reference in its/their entirety herein.

TECHNICAL FIELD

The present disclosure relates to compositions comprising cationic compounds having perfluorinated ether groups and reactive silane groups. More particularly, it relates to aqueous compositions comprising cationic compounds having perfluorinated ether groups and reactive silane groups, and methods for their use in protecting substrates.

BACKGROUND

Some fluorinated compounds have been shown to impart water repellency, oil repellency, or both to substrates such as, for example, textiles, paper, non-woven materials, leather, and masonry. Textiles have included natural fibers such as cotton, and synthetic fibers such as polyester. Paper substrates have included paper used for packaging food. Repellency has been achieved by applying a composition comprising a fluorinated compound to, for example, the surface of a substrate. In many cases, a fluorinated compound has been applied to the surface of a substrate in a composition comprising a substantial amount of an organic solvent. In some cases, the organic solvent has been flammable or combustible. In some cases, the organic solvent has comprised halogen-containing species such as tetrachloroethylene or trichlorotrifluoroethane. Methods to apply a composition comprising a fluorinated compound to a substrate have included spraying the solution from a pressurized container such as an aerosol can.

In many cases, compositions of fluorinated compounds have comprised organic, including halogen-containing, solvents, because the fluorinated compounds have had limited solubility in other solvents. However, for various reasons, there is awareness that the use of compositions comprising substantial amounts of flammable or combustible organic solvents may be less desirable. Similarly, there is awareness that the use of compositions comprising substantial amounts of halogen-containing solvents may be less desirable.

SUMMARY

We recognize that it has heretofore been difficult to develop compositions comprising fluorinated compounds and desirable solvents to impart, for example, water repellency, oil repellency, or both to a substrate. Thus, there is a need for compositions comprising fluorinated compounds, particularly cationic fluorinated compounds, that comprise or can be delivered from aqueous or substantially aqueous media and that can impart water and oil repellency to substrates and, more particularly, to surfaces of substrates.

In one aspect, the present invention provides a composition comprising at least one compound of Formula I:

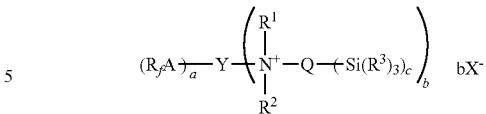

wherein a, b, and c are each independently an integer from about 1 to about 3; $R_f$ is a perfluorinated ether group; A is a linking group having the formula $-C_dH_{2d}ZC_gH_{2g}-$, wherein d and g are independently integers from about 0 to about 10 and Z is selected from the group consisting of a covalent bond, a carbonyl group, a sulfonyl group, a carboxamido group, a sulfonamido group, an iminocarbonyl group, an iminosulfonyl group, an oxycarbonyl group, a urea group, a urethane group, a carbonate group, and a carbonyloxy group; Y is a bridging group having about 1 to about 10 carbon atoms, a valency from about 2 to about 6, and comprising at least one of an alkylene group or an arylene group; Q is a connecting group having about 1 to about 10 carbon atoms, a valency from about 2 to about 6, and comprising at least one of an alkylene group or an arylene group; $R^1$ and $R^2$ are independently selected from the group consisting of a hydrogen atom, an alkyl group, an aryl group, and an aralkyl group; each $R^3$ is independently selected from the group consisting of hydroxy groups, alkoxy groups, acyl groups, acyloxy groups, halo groups, and polyether groups; and $X^-$ is a counter ion selected from the group consisting of inorganic anions, organic anions, and combinations thereof.

In some embodiments, the present invention provides a composition comprising at least one compound of Formula II:

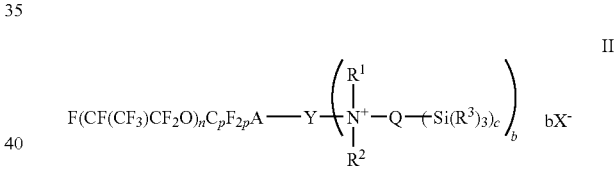

wherein n is an integer from about 2 to about 12; p is an integer from about 1 to about 6; b and c are each independently an integer from about 1 to about 3; A is a linking group having the formula $-C_dH_{2d}ZC_gH_{2g}-$, wherein d and g are independently integers from about 0 to about 10 and Z is selected from the group consisting of a covalent bond, a carbonyl group, a sulfonyl group, a carboxamido group, a sulfonamido group, an iminocarbonyl group, an iminosulfonyl group, an oxycarbonyl group, a urea group, a urethane group, a carbonate group, and a carbonyloxy group; Y is a bridging group comprising an alkylene group having about 1 to about 6 carbon atoms; Q is a connecting group comprising an alkylene group having about 1 to about 6 carbon atoms; $R^1$ and $R^2$ are independently alkyl groups having about 1 to about 4 carbon atoms; each $R^3$ is independently selected from the group consisting of hydroxy groups, methoxy groups, ethoxy groups, acetoxy groups, chloro groups, and polyether groups; and $X^-$ is a counter ion selected from the group consisting of a halide, sulfate, phosphate, an alkanoate, an alkyl sulfonate, an aryl sulfonate, an alkyl phosphonate, an aryl phosphonate, a fluorinated alkanoate, a fluorinated alkyl sulfonate, a fluorinated aryl sulfonate, a fluorinated alkyl sulfonimide, a fluorinated alkyl methide, and combinations thereof.

The compositions of the invention are useful for protecting a substrate, including imparting water repellency, oil repellency, or both to a substrate. In particular, compositions of the invention are useful for imparting water repellency, oil repellency, or both to at least one surface of a substrate. The compositions of the invention may be grafted or blended to a nanoparticle containing a functional group compatible with the silane group. In one aspect, the nanoparticle includes a hydroxyl functional group. In one aspect, the nanoparticle is a silica, titanium, or zirconium nanoparticle.

In another aspect, the present invention provides a method of protecting a surface, the method comprising 1) providing a composition comprising a compound of Formula I or Formula II, and 2) contacting a substrate with the composition. In one aspect, the composition may be grafted or blended to a nanoparticle containing a functional group compatible with the silane group of Formula I or Formula II prior to contact with a substrate. The substrate may include ceramic, textile, silicate, paper, metal, wood, and plastic.

In another aspect, the present invention provides a kit comprising a) a composition comprising a compound of Formula I, and b) instructions for using the kit.

This summary is not intended to describe each and every embodiment or implementation of the present invention. Further embodiments, features, and advantages of the present invention will be apparent from the following detailed description thereof and from the claims.

DETAILED DESCRIPTION

In several places throughout the application, guidance is provided through lists of examples, which examples can be used in various combinations. In each instance, the recited list serves only as a representative group and should not be interpreted as an exclusive list.

As used herein,

Any recitation of numerical ranges by endpoints includes all numbers subsumed within that range (e.g., 1 to 5 includes 1, 1.5, 2, 2.75, 3, 3.80, 4, 5, etc.);

The terms "a," "an," "the," "at least one," and "one or more" are used interchangeably. Thus, for example, a composition that comprises "a" compound of Formula I can be interpreted to mean that the composition includes "one or more" compounds of Formula I;

The term "perfluorinated ether group" refers to an ether group having at least one fluorine-to-carbon bond and being substantially free of hydrogen-to-carbon bonds;

The term "perfluoropolyether group" refers to a perfluorinated ether group comprising more than one perfluorinated ether group;

The term "perfluoroalkyl group" refers to an alkyl group having at least one fluorine-to-carbon bond and being substantially free of hydrogen-to-carbon bonds; and The term "perfluoroalkylene group" refers to an alkylene group having at least one fluorine-to-carbon bond and being substantially free of hydrogen-to-carbon bonds.

In one aspect, the present invention provides a composition comprising at least one compound of Formula I:

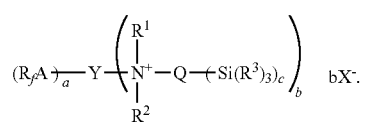

(I)

Perfluorinated Ether Group $R_f$

The monovalent perfluorinated ether group comprises at least 1 carbon atom. The perfluorinated ether group may be a linear perfluorinated ether group, or it may comprise branched or cyclic structures. An oxygen atom in the perfluorinated ether group may be in one or more linear, branched, or cyclic structures. The perfluorinated ether group may have a weight average molecular weight of about 200 to about 7000, about 500 to about 5000, about 1000 to about 5000, about 1000 to about 4000, about 1000 to about 3000, or about 1000 to 1500. In some embodiments, the perfluorinated ether group has a weight average molecular weight of about 300, about 400, about 600, about 800, about 1000, about 1200, about 1400, about 1600, about 1800, about 2000, about 2200, about 2400, about 2600, about 2800, or about 3000.

The perfluorinated ether group may comprise a perfluoroalkyl group, a perfluoroalkylene group, or both. The perfluoroalkyl group may comprise linear, branched, or cyclic structures, or a combination of such structures. In some embodiments, the perfluoroalkyl group comprises more than one of a linear, branched, or cyclic structure. Non limiting examples of perfluoroalkyl groups include perfluoromethyl, perfluoroethyl, perfluoropropyl, perfluorobutyl, perfluoro-2-butyl, perfluorohexyl, and perfluorocyclohexyl, perfluorocyclohexylmethyl groups. The perfluoroalkylene group may comprise linear, branched, or cyclic structures, or a combination of such structures. In some embodiments, the perfluoroalkylene group comprises more than one of a linear, branched, or cyclic structure. Non limiting examples of perfluoroalkylene groups include perfluoromethylene, perfluoroethylene, and perfluoro-1,2-propylene.

In some embodiments, the perfluorinated ether group is a perfluoropolyether group comprising at least two oxygen atoms.

The perfluorinated ether group may comprise a structure $F(C_mF_{2m}O)_nC_pF_{2p}$—, wherein m is an integer of at least about 1, n is an integer of at least about 2, and p is an integer of at least about 1. It is understood that the preparation of perfluorinated ethers comprising such structures may result in a mixture of perfluorinated ethers, each comprising structures having different integer values of m, n, and p. Such mixtures of perfluorinated ethers may have non-integer average values of m, n and p. In some embodiments, m is an integer from about 1 to about 12, n is an integer from about 2 to about 10, and p is an integer from about 1 to about 6. In some embodiments, m is an integer greater than about 2, greater than about 4, greater than about 6, greater than about 8, or greater than about 10. In some embodiments, n is an integer greater than about 2. In some embodiments, n is an integer greater than about 3, greater than about 4, greater than about 5, greater than about 6, greater than about 7, greater than about 8, or greater than about 9. In some embodiments, p is an integer from about 1 to about 10, about 1 to about 8, or about 1 to about 6. In some embodiments, p is an integer of 1, 2, 3, 4, 5, 6, 7, 8, 9, or 10. The substructures —$C_mF_{2m}$— and —$C_pF_{2p}$— may independently comprise one or more of a linear, branched, or cyclic structure.

The perfluorinated ether group may comprise a structure $F(CF(CF_3)CF_2O)_qCF(CF_3)$—, wherein q is an integer greater than about 1. It is understood that the preparation of perfluorinated ethers comprising such structures may result in a mixture of perfluorinated ethers each comprising structures having different integer value of q. Such mixtures of perfluorinated ethers may have non-integer average values of q. In some embodiments, q is an integer greater than about 2, greater than about 3, greater than about 4, greater than about 5, greater than about 6, greater than about 7, greater than about 8, greater than about 9, greater than about 10, greater than about 15, greater than about 20, or greater than about 25. In some embodiments, q is an integer from about 2 to about 12. The perfluorinated ether group may be derived from, for example, tetrafluoroethylene or hexafluoropropylene, as described in, for example, U.S. Pat. Nos. 3,882,193 (Rice, et al.) and 3,250,807 (Fritz et al.). The perfluorinated ether group may be derived from, for example, hexafluoropropylene oxide, as described in, for example, U.S. Pat. Nos. 6,923,921 (Flynn, et al.) and 3,250,808 (Moore, Jr., et al.).

Linking Group A

Linking group A links the perfluorinated ether group $R_f$ to the bridging group Y. Linking group A has a valency at least sufficient to link the perfluorinated ether group $R_f$ to the bridging group Y. In some embodiments, linking group A has a valency of at least about 2. In some embodiments, linking group A has a valency of about 2. In some embodiments, linking group A has a valency from about 2 to about 6.

Linking group A may be formed as part of the perfluorinated ether group $R_f$, i.e., linking group A may be linked to perfluorinated ether group $R_f$ before it is linked to bridging group Y. Alternatively, linking group A may be formed as part of bridging group Y and may be linked to bridging group Y before it is linked to perfluorinated ether group $R_f$. Alternatively, linking group A may be formed during a chemical reaction of a perfluorinated ether precursor compound and a bridging group Y precursor compound. In this embodiment, linking group A may be linked to perfluorinated ether group $R_f$ and bridging group Y essentially at the same time. In some embodiments, linking group A may be divalent.

In some embodiments, the linking group A may have the formula $-C_dH_{2d}ZC_gH_{2g}-$, wherein d and g are independently integers from about 0 to about 10 and subgroup Z is selected from the group consisting of a covalent bond, a carbonyl group, a sulfonyl group, a carboxamido group, a sulfonamido group, an iminocarbonyl group, an iminosulfonyl group, an oxycarbonyl group, a urea group, a urethane group, a carbonate group, and a carbonyloxy group. In some embodiments, d and g are independently integers from about 1 to about 4, and Z is selected from the group consisting of a covalent bond, a carbonyl group, a sulfonyl group, a carboxamido group, a sulfonamido group, an iminocarbonyl group, an iminosulfonyl group, an oxycarbonyl group, a urea group, a urethane group, a carbonate group, and a carbonyloxy group. In some embodiments, for example when d and g are both zero, linking group A is comprises subgroup Z.

In some embodiments, for example when Z is a covalent bond, linking group A comprises an alkylene group. The alkylene group may comprise linear, branched, or cyclic structures. The alkylene group may further comprise at least one heteroatom, e.g., oxygen, nitrogen, or sulfur. The alkylene group may comprise at least about 1 carbon atom, or up to about 2, up to about 3, up to about 4, up to about 5, up to about 6, up to about 7, up to about 8, up to about 9, up to about 10, up to about 14, up to about 16, up to about 18, or up to about 20 carbon atoms. Non-limiting examples of alkylene groups include methylene, ethylene, 1,3-propylene, 1,2-propylene, 1,4-butylene, 1,4-cyclohexylene, and 1,4-cyclohexyldimethylene.

In some embodiments, linking group A further comprises an arylene group. The arylene group comprises one or more aromatic rings. When the arylene group comprises more than one aromatic ring, the aromatic rings (which may be the same or different) may be fused, joined by a covalent bond, or joined via, for example, a joining group such as an alkylene group or a heteroatom such as oxygen. The arylene group may comprise at least one heteroatom, e.g., oxygen, nitrogen, or sulfur. The arylene group may comprise at least about 4 carbon atoms, or at least about 5, at least about 6, at least about 10, or at least about 14 carbon atoms. Non-limiting examples of arylene groups include phenyl, 1-naphthyl, 2-naphthyl, 9-anthracenyl, furanyl, and thiophenyl.

In some embodiments, linking group A may comprise an aralkylene group. In some embodiments, linking group A may comprise an alkarylene group.

Bridging Group Y

Bridging group Y bridges the linking group A and the cationic nitrogen atom. Bridging group Y has a valency at least sufficient to bridge the linking group A and the cationic nitrogen atom. As shown in Formulae I and II, for example, bridging group Y may have a valency of at least about a+b. In some embodiments, bridging group Y has a valency of about 2. In some embodiments, bridging group Y has a valency of greater than about 2. In some embodiments, bridging group Y has a valency from about 2 to about 6. Bridging group Y may have a valency from about 2 to about 6, may comprise about 1 to about 10 carbon atoms, and may comprise at least one of an alkylene group or an arylene group.

Bridging group Y may be formed as part of a group comprising the cationic nitrogen atom. Alternatively, it may be formed as part of a group comprising a nitrogen atom that will be later quaternized to form the cationic nitrogen atom. Alternatively, it may be formed during a chemical reaction of a linking group A precursor compound and a nitrogen containing compound. In this embodiment, bridging group Y may bridge linking group A and a neutral or cationic nitrogen atom essentially at the same time. In some embodiments, bridging group Y may be divalent.

In some embodiments, bridging group Y comprises an alkylene group. The alkylene group may comprise linear, branched, or cyclic structures. The alkylene group may comprise at least one heteroatom, e.g., oxygen, nitrogen, or sulfur. The alkylene group may comprise at least about 1 carbon atom, or up to about 2, up to about 3, up to about 4, up to about 5, up to about 6, up to about 7, up to about 8, up to about 9, up to about 10, up to about 14, up to about 16, up to about 18, or up to about 20 carbon atoms. The alkylene group may comprise more than about 20 carbon atoms. Non-limiting examples of alkylene groups include methylene, ethylene, 1,3-propylene, 1,2-propylene, 1,4-butylene, 1,4-cyclohexylene, and 1,4-cyclohexyldimethylene.

In some embodiments, bridging group Y comprises an arylene group. The arylene group comprises one or more aromatic rings. When the arylene group comprises more than one aromatic ring, the aromatic rings (which may be the same or different) may be fused, joined by a covalent bond, or joined via, for example, a joining group such as an alkylene group or a heteroatom such as oxygen. The arylene group may comprise at least one heteroatom, e.g., oxygen, nitrogen, or sulfur. The arylene group may comprise at least about 4 carbon atoms, or at least about 5, at least about 6, at least about 10, or at least about 14 carbon atoms. Non-limiting examples of arylene groups include phenyl, 1-naphthyl, 2-naphthyl, 9-anthracenyl, furanyl, and thiophenyl.

In some embodiments, bridging group Y comprises an aralkylene group or an alkarylene group. The aralkylene or alkarylene group may comprise one or more aromatic rings. When the aralkylene or alkarylene group comprises more than one aromatic ring, the aromatic rings (which may be the same or different) may be fused, joined by a covalent bond, or joined via, for example, a joining group such as an alkylene group or a heteroatom such as oxygen. The aralkylene or alkarylene group may comprise at least one heteroatom, e.g., oxygen, nitrogen, or sulfur. The aralkylene or alkarylene group may comprise at least about 4 carbon atoms, or at least about 5, at least about 6, at least about 10, or at least about 14 carbon atoms.

Connecting Group Q

Connecting group Q connects the cationic nitrogen atom to the silicon atom. Connecting group Q has a valency at least sufficient to connect the cationic nitrogen atom to the silicon atom. As shown in Formulae I and II, for example, connecting group Q has a valency of at least about c+1. In some embodiments, connecting group Q has a valency of about 2. In some embodiments, connecting group Q has a valency of greater than about 2. In some embodiments, connecting group Q has a valency from about 2 to about 6. Connecting group Q may have a valency from about 2 to about 6, may comprise about 1 to about 10 carbon atoms, and may comprise at least one of an alkylene group or an arylene group.

Connecting group Q may be formed as part of a group comprising the cationic nitrogen atom. Alternatively, it may be formed as part of a group comprising a silicon atom. Alternatively, it may be formed during a chemical reaction of a nitrogen containing compound and a silicon containing compound. In this embodiment, connecting group Q connects a neutral or cationic nitrogen atom and a silicon atom essentially at the same time. In some embodiments, connecting group Q may be divalent.

In some embodiments, connecting group Q comprises an alkylene group. The alkylene group may comprise linear, branched, or cyclic structures. The alkylene group may comprise at least one heteroatom, e.g., oxygen, nitrogen, or sulfur. The alkylene group may comprise at least about 1 carbon atom, or up to about 2, up to about 3, up to about 4, up to about 5, up to about 6, up to about 7, up to about 8, up to about 9, up to about 10, up to about 14, up to about 16, up to about 18, or up to about 20 carbon atoms. In some embodiments, connecting group Q comprises at least one oxyalkylene group. In some embodiments, connecting group Q comprises a poly(oxyalkylene) group, for example, a poly(oxyethylene) group. The alkylene group may comprise more than about 20 carbon atoms. Non-limiting examples of alkylene groups include methylene, ethylene, 1,3-propylene, 1,2-propylene, 1,4-butylene, 1,4-cyclohexylene, and 1,4-cyclohexyldimethylene.

In some embodiments, connecting group Q comprises an arylene group. The arylene group comprises one or more aromatic rings. When the arylene group comprises more than one aromatic ring, the aromatic rings (which may be the same or different) may be fused, joined by a covalent bond, or joined via, for example, a joining group such as an alkylene group or a heteroatom such as oxygen. The arylene group may comprise at least one heteroatom, e.g., oxygen, nitrogen, or sulfur. The arylene group may comprise at least about 4 carbon atoms, or at least about 5, at least about 6, at least about 10, or at least about 14 carbon atoms. Non-limiting examples of arylene groups include phenyl, 1-naphthyl, 2-naphthyl, 9-anthracenyl, furanyl, and thiophenyl.

In some embodiments, connecting group Q comprises an aralkylene or an alkarylene group. The aralkylene or alkarylene group may comprise one or more aromatic rings. When the aralkylene or alkarylene group comprises more than one aromatic ring, the aromatic rings (which may be the same or different) may be fused, joined by a covalent bond, or joined via, for example, a joining group such as an alkylene group or a heteroatom such as oxygen. The aralkylene or alkarylene group may comprise at least one heteroatom, e.g., oxygen, nitrogen, or sulfur. The aralkylene or alkarylene group may comprise at least about 4 carbon atoms, or at least about 5, at least about 6, at least about 10, or at least about 14 carbon atoms.

$R^1$, $R^2$, and $R^3$

In the compounds of Formulae I and II, $R^1$ and $R^2$ are bonded to the cationic nitrogen atom. Each $R^1$ and $R^2$ may be independently selected from the group consisting of a hydrogen atom, an alkyl group, an aryl group and an aralkyl group.

When either or both of $R^1$ or $R^2$ is an alkyl group, the alkyl group may comprise about 1 carbon atom, more than about 1 carbon atom, more than about 2 carbon atoms, more than about 4 carbons atoms, more than about 6 carbon atoms, more than about 8 carbon atoms, more than about 10 carbon atoms, more than about 16 carbon atoms, or more than about 20 carbon atoms. In some embodiments, the alkyl group comprises 1 to 8 carbon atoms. In some embodiments, the alkyl group comprises a straight chain alkyl group. In other embodiments, the alkyl group comprises a branched alkyl group. In still other embodiments, the alkyl group comprises a cyclic alkyl group. When each of $R^1$ and $R^2$ comprises an alkyl group, $R^1$ and $R^2$ may comprise the same alkyl group, or $R^1$ and $R^2$ may comprise different alkyl groups. Non-limiting examples of alkyl groups include methyl, ethyl, 1-propyl, iso-propyl, butyl, iso-butyl, sec-butyl, pentyl, iso-pentyl, neo-pentyl, hexyl, 2-ethylhexyl, octyl, decyl, undecyl, dodecyl, tetradecyl, pentadecyl, octadecyl, cyclohexyl, 4-methylcyclohexyl, cyclohexylmethyl, cyclopenyl, and cyclooctyl.

When either or both of $R^1$ or $R^2$ is an aryl group, the aryl group may comprise one arene ring or more than one arene ring. Arene rings may comprise up to 6 carbon atoms, up to 8 carbon atoms, up to 10 carbon atoms, up to 12 carbon atoms, up to 14 carbon atoms, up to 16 carbon atoms, or up to 18 carbon atoms. Arene rings may comprise a heteroatom, for example, nitrogen, oxygen, or sulfur. If more than one arene ring is present in an aryl group, the arene rings may be fused together, or they may be joined by a chemical bond. When each of $R^1$ and $R^2$ comprises an aryl group, $R^1$ and $R^2$ may comprise the same aryl group or different aryl groups. Non-limiting examples of aryl groups include substituted and unsubstituted phenyl, 1-naphthyl, 2-naphthyl, 9-anthracenyl, and biphenyl.

When either or both of $R^1$ or $R^2$ are an aralkyl group, the aralkyl group may comprise one arene ring or more than one arene ring. The aralkyl group may comprise up to 6 carbon atoms, up to 8 carbon atoms, up to 10 carbon atoms, up to 12 carbon atoms, up to 14 carbon atoms, up to 16 carbon atoms, up to 18 carbon atoms, or up to 20 carbon atoms. If more than one arene ring is present in the aralkyl group, the arene rings may be fused together, or they may be joined by a chemical bond. Arene rings may comprise a heteroatom, for example, nitrogen, oxygen, or sulfur. When each of $R^1$ and $R^2$ comprises an aralkyl group, $R^1$ and $R^2$ may comprise the same aralkyl group, or $R^1$ and $R^2$ may comprise different aralkyl groups. Non-limiting examples of aralkyl groups include benzyl, 1-phenylethyl, 2-phenylethyl, 3-phenylpropyl, 2-naphthylethyl, and 9-anthracenylmethyl.

In the compounds of Formulae I and II, each $R^3$ is independently bonded to the silicon atom. In some embodiments, each $R^3$ is independently selected from the group consisting of hydroxy groups, alkoxy groups, acyl groups, acyloxy groups, halo groups, and polyether groups. In some embodiments, at least one $R^3$ is independently bonded to the silicon atom via a hydrolyzable bond. In this context, "bonded via a hydrolyzable bond" refers to the reactivity of the $R^3$-silicon bond with water, i.e., to a bond that is capable of undergoing a hydrolysis reaction. In some embodiments, $R^3$ is bonded to the silicon atom via a bond including a carbon atom, i.e., $R^3$ comprises a carbon atom bonded to the silicon atom. In some embodiments, $R^3$ is bonded to the silicon atom via a bond including an atom other than a carbon atom. In some embodiments, $R^3$ is bonded to the silicon atom via a bond including an oxygen atom, i.e., $R^3$ comprises an oxygen atom bonded to the silicon atom. In some embodiments, $R^3$ is bonded to the silicon atom via a bond including a nitrogen atom, i.e., $R^3$ comprises a nitrogen atom bonded to the silicon atom.

Each $R^3$ may independently be a non-ionic group or an ionic group. The ionic group may be cationic, anionic, or zwitterionic. Non-limiting examples of non-ionic groups include hydroxy, alkoxy, acyl, acyloxy, halo, and polyether groups. Alkoxy groups include, for example, methoxy and ethoxy groups. Halo groups include, for example, chloro, bromo, and iodo groups. Acyl groups include, for example, acetyl, propionyl, and benzoyl groups. Acyloxy groups include, for example, acetoxy and propionoxy groups. Polyether groups may comprise oxyalkylene groups, for example groups having the formula $(OC_vH_{2v})$, where v is an integer from about 1 to about 6. Non-limiting examples of polyether groups comprising oxyalkylene groups include poly(oxymethylene), poly(oxyethylene), and poly(oxybutylene) groups. In some embodiments, the polyether group comprises about 1 to about 200 oxyalkylene groups. In some embodiments, the polyether group comprises about 1 to about 5, about 1 to about 10, about 1 to about 20, about 1 to about 30, about 1 to about 40, or about 1 to about 50 oxyalkylene groups.

Non-limiting examples of ionic groups include groups such as $-OCH_2CH_2N^+(CH_3)_3I^-$, $-OCH_2CH_2N^+(CH_3)_3Cl^-$, and $-OCH_2CH_2N^+(CH_3)_2CH_2CH_2CH_2SO_3^-$. In some embodiments, polyether groups comprising more than one oxyalkylene group further comprises a cationic group (e.g., a group comprising a cationic nitrogen atom), an anionic group, or both a cationic group and an anionic group.

Counter Ion $X^-$

Counter ion $X^-$ may comprise an organic anion, an inorganic anion, or a combination of organic and inorganic anions. In some embodiments, counter ion $X^-$ may result from a chemical reaction that forms the cationic nitrogen atom, for example a reaction between an amine and an alkylating agent such as, for example, a chloroalkylsilane, that forms a nitrogen to carbon bond and displaces a chloride ion. In some embodiments, counter ion $X^-$ may result from the protonation of an amine with an acid. Such a reaction can provide a cationic nitrogen atom and the conjugate base of the acid (i.e., the counter ion $X^-$). In some embodiments, counter ion $X^-$ may result from an ion exchange reaction, e.g., a reaction in which one anion is exchanged for another.

In some embodiments, counter ion $X^-$ may be selected from the group consisting of a halide (e.g., chloride, bromide, or iodide), sulfate, phosphate, an alkanoate (e.g., acetate or propionate), an alkyl sulfonate, an aryl sulfonate (e.g., benzenesulfonate), an alkyl phosphonate, an aryl phosphonate, a fluorinated alkanoate (e.g., trifluoroacetate), a fluorinated alkyl sulfonate (e.g., trifluormethanesulfonate), a fluorinated aryl sulfonate (e.g., 4-fluorophenylsulfonate), a fluorinated alkyl sulfonimide (e.g., bis(trifluoromethylsulfonyl)imide, a fluorinated alkyl methide (e.g., tris(trifluoromethylsulfonyl) methide, and combinations thereof.

Solvents

The compositions of the invention may comprise at least one water-soluble organic solvent. The compositions of the invention may comprise less than about 1 weight percent to more than about 99 weight percent water-soluble organic solvent. The compositions may comprise less than about 1 weight percent, more than about 1 weight percent, more than about 5 weight percent, more than about 10 weight percent, more than about 20 weight percent, more than about 30 weight percent, more than about 40 weight percent, more than about 50 weight percent, more than about 60 weight percent, more than about 70 weight percent, more than about 80 weight percent, more than about 90 weight percent, or more than about 99 weight percent water soluble organic solvent.

The water-soluble organic solvent may be soluble in water in all proportions of organic solvent and water. The water-soluble organic solvent may be soluble in water up to about 1 weight percent, up to about 2 weight percent, up to about 5 weight percent, up to about 10 weight percent, up to about, 20 weight percent, up to about 30 weight percent, up to about 40 weight percent, up to about 50 weight percent, up to about 60 weight percent, up to about 70 weight percent, up to about 80 weight percent, or up to about 90 weight percent organic solvent in water. The water-soluble organic solvent may be soluble in water up to more than about 90 weight percent organic solvent in water. Suitable organic solvents include ketones (e.g., acetone), ethers (e.g., dimethoxyethane, tetrahydrofuran), esters (e.g., methyl acetate), carbonates (e.g., propylene carbonate), amides (e.g., dimethylacetamide), sulfoxides (e.g., dimethylsulfoxide), sulfones (e.g., sulfolane), and alcohols (e.g., ethanol, isopropanol, n-propanol). In some embodiments, the water-soluble organic solvent comprises one or more of butoxyethanol, methoxyethanol, propylene glycol monopropyl ether, and 1-methoxy-2-propanol. In some embodiments, the water-soluble organic solvent comprises a solvent used to prepare a compound of Formula I or Formula II. In some embodiments, the water-soluble comprises a solvent not used to prepare a compound of Formula I or Formula II, for example a solvent that may be added to the composition. In some embodiments, the water-soluble organic solvent may be added to the composition during a processing or formulation step, for example during a solvent exchange process.

The composition of the invention may comprise water. Water may be present from less than about 1 to more than about 99 weight percent of the composition. In some embodiments, water is present at more than about 1 weight percent, or more than about 10, more than about 20, more than about 30, more than about 40, more than about 50, more than about 60, more than about 70, more than about 80, more than about 90, more than about 95, more than about 97, more than about 98, or more than about 99 weight percent of the composition.

The composition of the invention may comprise water and a water-soluble organic solvent. The weight ratio of water to water-soluble organic solvent may be from less than 1 to 99 to more than 99 to 1. In some embodiments, the weight ratio of water to water-soluble organic solvent can be at least about 1 to about 99, about 2 to about 98, about 5 to about 95, about 10 to about 90, about 15 to about 85, about 20 to about 80, about 30 to about 70, about 40 to about 50, about 50 to about 50, about 60 to about 40, about 70 to about 30, about 80 to about 20, about 90 to about 10, about 95 to about 5, about 98 to about 2, or about 99 to about 1.

The concentration of a compound of Formula I or Formula II in a mixture of water and a water soluble organic solvent may be less than about 99 weight percent, less than about 90 weight percent, less than about 80 weight percent, less than about 70 weight percent, less than about 60 weight percent, less than about 50 weight percent, less than about 40 weight percent, less than about 30 weight percent, less than about 20 weight percent, or less than about 10 weight percent. In some embodiments, concentration of a compound of Formula I or Formula II in a mixture of a water soluble organic solvent and water is less than about 9, less than about 8, less than about 7, less than about 6, less than about 5, less than about 4, less than about 3, less than about 2, less than about 1, or less than about 0.5 weight percent. In various embodiments, the weight ratio of water to water-soluble organic solvent is more than about 90 to about 10, and the concentration of at least one compound of Formula I or Formula II in a mixture of a water soluble organic solvent and water is less than about 10 weight percent, less than about 6 weight percent, less than about 4 weight percent, less than about 2 weight percent, or less than about 1 weight percent.

Optional Additives

The compositions of the invention may comprise one or more additives. Such additives may include, for example, UV absorbers, buffering agents, fireproofing agents, antimicrobial agents (e.g., fungicidal agents), or mineral salts.

Stability

The compositions of the invention, particularly compositions comprising water, may exhibit stability at room temperature (i.e., at about 25° C.) for periods of up to one day, up to one week, up to two weeks, up to three weeks, up to one month, up to three months, up to six months, up to one year, up to two years, or up to three years. The compositions may exhibit such stability at temperatures up to 50° C. As used herein, the term "stability" refers to a property of compositions of the invention, particularly compositions comprising water, to remain substantially physically unchanged, i.e., free of, for example, substantial precipitate or substantial gel, for periods of time. In some embodiments, stability may be assessed by visually observing a sample of a composition for the formation of precipitate or gel over a period of time, e.g., over a storage time. It is recognized that, as prepared, compositions of the invention may have a small amount of precipitate or gel, or both, but this small amount does not substantially increase over time.

Method and Kit

The present invention provides a method of protecting a surface, the method comprising 1) providing a composition comprising a compound of Formula I, and 2) contacting a substrate with the composition. In one aspect, the composition may be grafted or blended to a nanoparticle containing a functional group compatible with the silane group of Formula I or Formula II prior to contact with a substrate. In one aspect, the nanoparticle includes a hydroxyl functional group. In one aspect, the nanoparticle is silica, titanium or zirconium nanoparticle.

The step of contacting may comprise immersing, spraying, brushing, rolling, flooding, or condensing. The substrate may include ceramic, textile, silicate, paper, metal, wood, and plastic. In some embodiments, the substrate may be cotton, viscose, wool, silk, polyester, polyamide, styrene polymers and copolymers, cellulose acetate, rayon, clay, ceramic, glass, concrete, and combinations thereof. In some embodiments, the method comprises contacting a substrate with a composition comprising at least one compound of Formula I or Formula II, at least one water soluble organic solvent, and water.

The substrate may comprise ceramic. Such ceramic may be in the form of, for example glazed or unglazed ceramic tile (e.g., kitchen or bathroom tile). The substrate may comprise glass, for example fiberglass, flint glass or borosilicate glass. The substrate may comprise concrete, including, for example, structural concrete and decorative concrete. In some embodiments, the substrate may be a textile comprising a blend of cotton and polyester or a blend of polyamide and polyester. In some embodiments, the substrate comprises a textile such as for use in clothing or upholstery.

The step of contacting may be carried out at room temperature (i.e., at about 25° C.) or at elevated temperature. In some embodiments, the method comprises the step of heating the substrate before contacting it with a composition of the invention. In some embodiments, the method comprises the step of heating the substrate after contacting it with a composition of the invention. Heating the substrate after contacting it with a composition of the invention may increase the rate of evaporation of the solvents.

The compositions of the invention can be used to protect a substrate, particularly the surface of a substrate, so as to render the substrate water repellent, oil repellent, or both, or to provide soil and/or stain repellency to the substrate. Protection of a substrate may result in rendering the protected substrate, particularly the protected surface of a protected substrate, more readily cleanable due to the oil and/or water repellent nature of the protected substrate or surface. In some embodiments, a substrate is protected by an amount of a compound of Formula I or Formula II sufficient to result in the substrate having an advancing contact angle with deionized or distilled water of at least about 70° and an advancing contact angle with hexadecane of at least about 40°. A compound of Formula I or Formula II may react with a substrate to form an ionic or a covalent bond. In some embodiments, heating the substrate before or after contacting it with a composition of the invention may facilitate a reaction between a compound and the substrate.

When, for example, the substrate is a textile, the textile or the surface of the textile may be protected by an amount of a compound of Formula I or Formula II sufficient to result in the textile having repellency to water and/or to oil. The desired degree of repellency to water and/or to oil may depend, for example, on the intended end use of the textile. In some embodiments, the surface of the textile may be protected by an amount of a compound of Formula I or Formula II sufficient to provide resistance to water that is sprayed onto the textile, i.e., the protected textile can have a high "spray rating" value.

The method of protecting a surface may comprise combining a composition of the invention, particularly a composition comprising a water-soluble organic solvent, with water. A composition of the invention may be combined with water by adding water to the composition or by adding the composition to water. In some embodiments, the providing step comprises combining the composition with water. In some embodiments, combining a composition of the invention with water comprises diluting a composition of the invention with water.

In some embodiments, a substrate, or particularly the surface of a substrate, may be cleaned prior to contacting it with the composition of the invention. The substrate may be cleaned prior to contacting it with the composition of the invention, for example by washing the substrate with water or with an organic solvent.

In another aspect, the present invention provides a kit comprising a composition comprising a compound of Formula I. In some embodiments, the kit may comprise an applicator comprising a container, a sprayer, a brush, a roller, or combinations thereof. In some embodiments, the kit may comprise instructions for using the kit. The instructions may include instructions relating to, for example, combining a composition with water or diluting a composition with water. The instructions may further include information relating to the selection of a method to contact a substrate with a composition of the invention.

EXAMPLES

Unless otherwise noted, all solvents and reagents were or can be obtained from Sigma-Aldrich Corp., St. Louis, Mo.

Spray Rating (SR) Test Method

The spray rating of a treated substrate is a value indicative of the dynamic repellency of the treated substrate to water that impinges on the treated substrate. The repellency was measured by Test Method 22-1996, published in the 2001 Technical Manual of the American Association of Textile Chemists and Colorists (AATCC), and was expressed in terms of a 'spray rating' (SR) of the tested substrate. The spray rating was obtained by spraying 250 ml water on the substrate from a height of 15 cm. The wetting pattern was visually rated using a 0 to 100 scale, where 0 means complete wetting and 100 means no wetting at all.

Water Repellency (WR) Test Method

The water repellency (WR) of a substrate was measured using a series of water-isopropanol test liquids and was expressed in terms of the "WR" rating of the treated substrate. The WR rating corresponded to the most penetrating test liquid which did not penetrate or wet the substrate surface after 15 seconds exposure. Substrates which were penetrated by or were resistant only to 100% water (0% isopropanol), the least penetrating test liquid, were given a rating of 0, whereas substrates resistant to 100% isopropanol (0% water), the most penetrating test liquid, were given a rating of 10. Other intermediate ratings were calculated by dividing the percent isopropanol in the test liquid by 10, e.g., a treated substrate resistant to a 70%/30% isopropanol/water blend, but not to an 80%/20% blend, would be given a rating of 7.

Oil Repellency (OR) Test Method

The oil repellency of a substrate was measured by the American Association of Textile Chemists and Colorists (AATCC) Standard Test Method No. 118-1983, which test was based on the resistance of a treated substrate to penetration by oils of varying surface tensions. Treated substrates resistant only to Nujol® mineral oil (the least penetrating of the test oils) were given a rating of 1, whereas treated substrates resistant to n-heptane (the most penetrating of the test liquids) were given a rating of 8. Other intermediate values were determined by use of other pure oils or mixtures of oils, as shown in Table 1.

TABLE 1

Test Liquids for Oil Repellency (OR)

| AATCC Oil Repellency Rating Number | Compositions |
| --- | --- |
| 1 | Nujol ® |
| 2 | Nujol ®/n-Hexadecane 65/35 |
| 3 | n-Hexadecane |
| 4 | n-Tetradecane |
| 5 | n-Dodecane |
| 6 | n-Decane |
| 7 | n-Octane |
| 8 | n-Heptane |

Example 1

Preparation of a Compound of Formula I

A 500 mL round bottom flask, fitted with a magnetic stir bar, was charged with methyl ester terminated perfluoropolyether oligomer having a weight average molecular weight of approximately 1285 grams per mole (100 g; prepared essentially as described in U.S. Pat. No. 3,250,808 (Moore, Jr. et al.)), N,N-dimethylaminopropylamine (8.1 g), and tert-butyl methyl ether (100 g). The flask was fitted with a reflux condenser, and the mixture was stirred and heated to reflux. The progress of the reaction was monitored using infrared spectrophotometry. After approximately 12 hours, the mixture was allowed to cool to room temperature and was then vacuum filtered. The volatile components were removed using a rotary evaporator to afford a reaction intermediate.

Then a 50 mL round bottom flask, fitted with a magnetic stir bar, was charged with the reaction intermediate (1 g) and 3-chloropropyltrimethoxysilane (0.148 g). The flask was fitted with a reflux condenser, and the mixture was stirred and heated under a nitrogen atmosphere to a temperature of approximately 140° C. After approximately 12 hours, the mixture was allowed to cool to room temperature to afford the product. The $^1$H NMR spectrum of the product was consistent with the assigned structure.

Comparative Example 1

Preparation of a Fluoroaliphatic Ammonium Silane Compound

A 500 mL 3-neck round bottom flask, fitted with a mechanical stirrer and a nitrogen inlet tube connected to a bubbler, was charged with $C_6F_{13}CH_2CH_2OH$ (72.86 g; obtained from Clariant Corp., Mount Holly, N.C.), triethylamine (23.27 g), and tert-butyl methyl ether (121.29 g). The flask was cooled in an ice bath with the contents under a nitrogen atmosphere. The flask was fitted with an addition funnel, and then methanesulfonyl chloride (25.20 g) was added via the funnel over approximately 120 minutes. The mixture was allowed to warm to room temperature overnight. The mixture was then washed with aqueous 1N HCl (120 g) and then with 2 weight percent aqueous sodium carbonate (120 g). The mixture was dried over anhydrous magnesium sulfate. The mixture was then filtered. Solvent removal using a rotary evaporator afforded an intermediate product as a solid.

A 50 mL round bottom flask, fitted with a magnetic stir bar, was charged with the intermediate product (1 g) and 3-N,N-dimethylpropyltrimethoxysilane (0.4688 g). The mixture was stirred under a nitrogen atmosphere and was heated to approximately 80° C. for approximately 4 hours. The mixture was then allowed to cool to room temperature to afford the product.

Examples 2 and 3

Stability of Solutions

The stability of solutions of compositions comprising the products of Example 1 and Comparative Example 1 was evaluated. For Example 2, 25 milliliters of a solution of 1 weight percent of the product of Example 1 in a mixture of 99 parts by weight water and 1 part by weight isopropanol in a screw-cap glass vial was stored in an oven at 65° C. After one week, no gellation or precipitation was observed. After three weeks, no gellation or precipitation was observed. For Example 3, 25 milliliters of a solution of 1 weight percent of the product of Comparative Example 1 in water in a screw-cap glass vial was stored in an oven at 65° C. After one week, no gellation or precipitation was observed.

Examples 4-9

The oil repellency (OR), water repellency (WR), and spray rating (SR) of three fabrics sprayed with a solution of the compound of Example 1 were determined as described above. A 1 weight percent solution of the compound of Example 1 in a 1 volume percent mixture of isopropanol in water was sprayed onto each of a cotton fabric (style 400M, available from Testfabrics, Inc., West Pittiston, Pa.), a 65/35 polyester/cotton blend fabric (style 7436, available from Testfabrics, Inc., West Pittiston, Pa.), and a khaki color cotton twill fabric (available from Avondale Mills, Graniteville, S.C.) using an aerosol sprayer available under the trade designation PREVAL sprayer from Precision Valve Corp., Yonkers, N.Y. The fabrics were sprayed with 10 to 12 grams of solution each. For Examples 4-6, the sprayed fabrics were allowed to dry in air at room temperature overnight. For Examples 7-9, the sprayed fabrics were dried using an iron (dry; highest temperature setting). The ironed fabrics were allowed to stand at room temperature overnight before they were tested. The data are given in Table 2.

TABLE 2

Test Results for Examples 4-9.

| Example | Fabric | WR | OR | SR |
|---|---|---|---|---|
| 4 | 400M cotton | 3 | 5 | 50 |
| 5 | 65/35 poly/cotton | 3 | 5 | 50 |
| 6 | cotton twill - khaki | 0 | 4 | 0 |
| 7 | 400M cotton | 2 | 5 | 60 |
| 8 | 65/35 poly/cotton | 3 | 5 | 60 |
| 9 | cotton twill - khaki | 0 | 5 | 0 |

Examples 10-11 and Comparative Examples 2-3

Two fabrics (Example 10 and Comparative Example 2, the 65/35 polyester/cotton blend fabric; Example 11 and Comparative Example 3, the 400M cotton fabric) were each padded with a solution prepared by diluting a 50 weight percent solution of the compound of Example 1 in isopropanol with water (Examples 10-11) or with a solution prepared by diluting a commercially available fabric protector (available under the trade designation 3M PROTECTIVE CHEMICAL PM-930) with water to provide compositions that delivered 1.2 weight percent solids on fabric by pad application. Each padded fabric was dried in air at room temperature overnight. The oil repellency (OR), water repellency (WR), and spray rating (SR) of the fabrics were determined as described above. The data are given in Table 3.

TABLE 3

Test Results for Examples 10-11 and Comparative Examples 2-3.

| Example | Fabric | WR | OR | SR |
|---|---|---|---|---|
| 10 | 65/35 poly/cotton | 3 | 6 | 50 |
| 11 | 400M cotton | 0 | 5 | 50 |
| Comparative 2 | 65/35 poly/cotton | 1 | 5 | 0 |
| Comparative 3 | 400M cotton | 0 | 5 | 0 |

Example 12 and Comparative Examples 4-6

Dynamic Contact Angle Measurements

For each of Example 12 and Comparative Examples 4-5, two glass slides (each having a surface area of 19.35 square centimeters) were coated with a test solution. For Example 12, the glass slides were dipped into a 1 weight percent solution of the compound of Example 1 in a 5 weight percent solution of isopropanol in water. For Comparative Example 4, the glass slides were dipped into a 1 weight percent solution of the compound of Comparative Example 1 in a 5 weight percent solution of isopropanol in water. For Comparative Example 5, the glass slides were dipped into a fluoropolymer coating solution available under the trade designation 3M EASY CLEAN COATING ECC-1000 from 3M Company, St. Paul, Minn. For Comparative Example 6, an untreated glass slide was evaluated. Each glass slide was then rinsed with water and was allowed to dry overnight at room temperature. One set of glass slides (from each of Example 12 and Comparative Examples 4-6) were scrubbed ten times with a heavy duty scouring pad (available under the trade designation SCOTCH-BRITE from 3M Company, St. Paul, Minn.). The dynamic contact angles of water (deionized and filtered) and hexadecane (reagent grade) were measured on each surface using a Model VCA-2500XE video contact angle analyzer (obtained from AST Products Inc., Billerica, Mass.). The data are given in Table 4. In Table 4, the term "Coating Material" refers to the coating composition on the glass, "H" refers to hexadecane, "W" refers to water, "adv" refers to advancing contact angle, and "rec" refers to receding contact angle. For example, "W-adv" refers to the water advancing contact angle.

TABLE 4

Contact Angle Data for Example 12 and Comparative Examples 4-6.

| Example | Coating Material | W-adv | W-rec | H-adv | H-rec |
|---|---|---|---|---|---|
| 12 | Example 1 | 75° | 48° | 68° | 52° |
| 12 (scrubbed) | Example 1 | 73° | 45° | 62° | 43° |
| Comparative 4 | Comparative 1 | 97° | 63° | 54° | 45° |
| Comparative 4 (scrubbed) | Comparative 1 | 93° | 47° | 49° | 40° |
| Comparative 5 | ECC-1000 | 82° | 47° | 63° | 49° |
| Comparative 5 (scrubbed) | ECC-1000 | 80° | 65° | 55 | 49° |
| Comparative 6 | none | 0° | 0° | 0° | 0° |
| Comparative 6 (scrubbed) | none | 0° | 0° | 0° | 0° |

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A composition comprising at least one compound of Formula I:

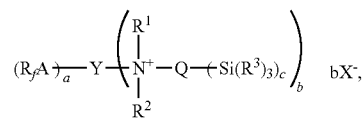

(I)

wherein
a, b, and c are independently integers from 1 to 3;
$R_f$ is a perfluorinated ether group;
A is a linking group having the formula $-C_dH_{2d}ZC_gH_{2g}-$, wherein d and g are independently integers from 0 to 10 and Z is selected from the group consisting of a covalent bond, a carbonyl group, a sulfonyl group, a carboxamido group, a sulfonamido group, an iminocarbonyl group, an iminosulfonyl group, an oxycarbonyl group, a urea group, a urethane group, a carbonate group, and a carbonyloxy group;

Y is a bridging group having 1 to 10 carbon atoms, a valency from 2 to 6, and comprising at least one of an alkylene group or an arylene group;

Q is a connecting group having 1 to 10 carbons atoms, a valency from 2 to 4, and comprising at least one of an alkylene group or an arylene group;

$R^1$ and $R^2$ are independently selected from the group consisting of a hydrogen atom, an alkyl group, an aryl group, and an aralkyl group;

each $R^3$ is independently selected from the group consisting of hydroxy groups, alkoxy groups, acyl groups, acyloxy groups, halo groups, and polyether groups; and $X^-$ is a counter ion selected from the group consisting of inorganic anions, organic anions, and combinations thereof.

2. The composition of claim 1 further comprising a water-soluble organic solvent.

3. The composition of claim 2 wherein the water-soluble organic solvent is selected from the group consisting of alcohols, ketones, and ethers.

4. The composition of claim 1 further comprising water.

5. The composition of claim 1 wherein the perfluorinated ether group is a perfluoropolyether group.

6. The composition of claim 1 wherein the perfluorinated ether group has a weight average molecular weight of at least about 1000.

7. The composition of claim 1 wherein the counter ion $X^-$ is selected from the group consisting of a halide, sulfate, phosphate, an alkanoate, an alkyl sulfonate, an aryl sulfonate, an alkyl phosphonate, an aryl phosphonate, a fluorinated alkanoate, a fluorinated alkyl sulfonate, a fluorinated aryl sulfonate, a fluorinated alkyl sulfonimide, a fluorinated alkyl methide, and combinations thereof.

8. The composition of claim 1 wherein at least one of d or g is at least 1, and Z is a covalent bond.

9. The composition of claim 1 wherein the bridging group Y comprises an alkylene group having 1 to 6 carbon atoms.

10. The composition of claim 1 wherein the connecting group Q comprises an alkylene group having 1 to 6 carbon atoms.

11. The composition of claim 1 wherein $R^1$ and $R^2$ are independently a hydrogen atom or an alkyl group having 1 to 8 carbon atoms.

12. The composition of claim 1 wherein the perfluorinated ether group has the structure $F(C_mF_{2m}O)_nC_pF_{2p}-$, wherein m is an integer from 1 to 12, n is an integer from 2 to 10, and p is an integer from 1 to 6.

13. The composition of claim 1 wherein the perfluorinated ether group has the structure $F(CF(CF_3)CF_2O)_qCF(CF_3)-$, wherein q is an integer from 2 to 12.

14. The composition of claim 1 wherein the composition is in a form selected from the group consisting of a liquid, a solid, a solution, a foam, a dispersion, a suspension, and an emulsion.

15. A method of protecting a surface, the method comprising:
1) providing a composition according to claims 1; and
2) contacting a substrate with the composition.

16. The method of claim 15 wherein the providing step comprises combining the composition with water.

17. The method of claim 15 wherein the providing step further comprises grafting or blending the composition with a nanoparticle containing a functional group compatible with the silane group.

18. The method of claim 15 wherein the substrate is selected from the group consisting of ceramic, textile, silicate, paper, metal, wood, and plastic.

19. A composition comprising at least one compound of Formula II

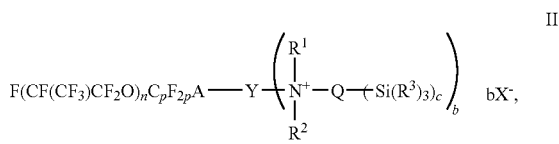

wherein
n is an integer from 2 to 12;
p is an integer from 1 to 6;
b and c are independently integers from 1 to 3;
A is a linking group having the formula $-C_dH_{2d}ZC_gH_{2g}-$, wherein d and g are independently integers from 0 to 10 and Z is selected from the group consisting of a covalent bond, a carbonyl group, a sulfonyl group, a carboxamido group, a sulfonamido group, an iminocarbonyl group, an iminosulfonyl group, an oxycarbonyl group, a urea group, a urethane group, a carbonate group, and a carbonyloxy group;

Y is a bridging group comprising an alkylene group having 1 to 6 carbon atoms;

Q is a connecting group comprising an alkylene group having 1 to 6 carbon atoms;

$R^1$ and $R^2$ are independently alkyl groups having 1 to 4 carbon atoms;

each $R^3$ is independently selected from the group consisting of hydroxy groups, methoxy groups, ethoxy groups, acetoxy groups, chloro groups, and polyether groups; and $X^-$ is a counterion selected from the group consisting of a halide, sulfate, phosphate, an alkanoate, an alkyl sulfonate, an aryl sulfonate, an alkyl phosphonate, an aryl phosphonate, a fluorinated alkanoate, a fluorinated alkyl sulfonate, a fluorinated aryl sulfonate, a fluorinated alkyl sulfonimide, a fluorinated alkyl methide, and combinations thereof.

20. The composition of claim 19 further comprising a water-soluble organic solvent.

21. The composition of claim 20 wherein the water-soluble organic solvent is selected from the group consisting of alcohols, ketones, and ethers.

22. The composition of claim 19 further comprising water.

23. The composition of claim 1 or 19 wherein d and g are independently integers from one to four, and Z is selected from the group consisting of a covalent bond, a carbonyl group, a sulfonyl group, a carboxamido group, a sulfonamido group, a urea group, a urethane group, and a carbonyloxy group.

24. The composition of claim 1 or 19 wherein the bridging group Y comprises a propylene group, the connecting group Q comprises a propylene group, b is 1, and c is 1.

25. The composition of claim 1 or 19 wherein the composition is grafted or blended with a nanoparticle containing a functional group compatible with the silane group.

* * * * *